United States Patent [19]

Kienzle

[11] Patent Number: 5,045,567
[45] Date of Patent: Sep. 3, 1991

[54] PROPANOLAMINE DERIVATIVES HAVING ANTI-DIABETIC EFFECTS

[75] Inventor: Frank Kienzle, Fluh, Switzerland

[73] Assignee: Hoffmann-La Roche Inc., Nutley, N.J.

[21] Appl. No.: 608,610

[22] Filed: Oct. 31, 1990

Related U.S. Application Data

[63] Continuation of Ser. No. 363,242, Jun. 8, 1989, abandoned.

[30] Foreign Application Priority Data

Jun. 10, 1989 [CH] Switzerland ............... 2245/88

[51] Int. Cl.$^5$ ............... A61K 31/24; A61K 31/135; C07C 229/34; C07C 215/08
[52] U.S. Cl. .................. 514/539; 514/95; 514/357; 514/567; 514/653; 546/334; 546/335; 549/75; 560/42; 562/451; 564/336; 564/355
[58] Field of Search .......... 560/42; 562/451; 514/539, 567

[56] References Cited

U.S. PATENT DOCUMENTS

| | | | |
|---|---|---|---|
| 3,804,899 | 4/1974 | Ebnother et al. | 564/361 |
| 4,585,796 | 4/1986 | Alig et al. | 514/620 |
| 4,692,465 | 9/1987 | Hindley et al. | 514/567 |
| 4,743,604 | 5/1988 | Alig et al. | 514/252 |
| 4,800,206 | 1/1989 | Alig et al. | 514/332 |
| 4,803,293 | 2/1989 | Berge et al. | 560/42 |
| 4,820,717 | 4/1989 | Mosse et al. | 514/653 |
| 4,871,755 | 10/1989 | Alig et al. | 514/376 |
| 4,892,886 | 1/1990 | Alig et al. | 560/42 |

FOREIGN PATENT DOCUMENTS

| | | | |
|---|---|---|---|
| 7208391 | 12/1972 | Netherlands | 574/653 |
| 8400956 | 3/1984 | World Int. Prop. O. | 564/355 |

OTHER PUBLICATIONS

Jen et al., Adrenergic Agents, J. Med. Chem., vol. 20, No. 5, 693–698 (1977).
Kienzle, F., CA, vol. 112, 234956z, 1990.

*Primary Examiner*—Glennon H. Hollrah
*Assistant Examiner*—S. Treanor
*Attorney, Agent, or Firm*—George M. Gould; Bernard S. Leon; George W. Johnston

[57] ABSTRACT

Propanolamine derivatives of the formula

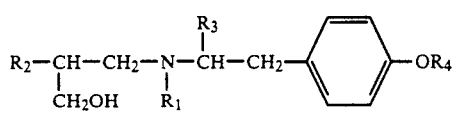

wherein
$R^1$ is hydrogen or a group of formula

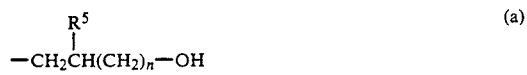

n is the number 0 or 1;
$R^2$ and $R^5$ are phenyl, m-halophenyl, m-trifluoromethylphenyl, thienyl or pyridyl;
$R^3$ is hydrogen or methyl;
$R^4$ is hydrogen, —$CH_2COOH$, —$CH_2COO$—$C_{1-4}$-alkyl, —$(CH_2)_2O$—$C_{1-4}$-alkyl or —$(CH_2)_2O(CH_2)_{1-4}$—$C_6H_5$;
and a physiologically compatible salt thereof.

The invention also relates to processes for the preparation of these propanolamine derivatives, pharmaceutical preparations and feedstuffs containing them, and methods of using the propanolamine derivatives.

20 Claims, No Drawings

PROPANOLAMINE DERIVATIVES HAVING ANTI-DIABETIC EFFECTS

This application is a continuation of application Ser. No. 07/363,242, filed 6/8/89 now abandoned.

FIELD OF THE INVENTION

The present invention is concerned with novel propanolamine derivatives which are useful for the treatment of obesity of diabetes mellitus and of conditions which are associated with high protein breakdown. Furthermore, the novel propanolamine derivatives may be incorporated into feedstuffs for fattening animals.

SUMMARY OF THE INVENTION

The propanolamine derivatives of the present invention are compounds of formula

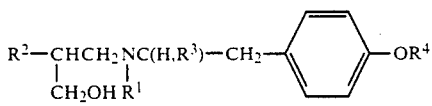

I wherein
$R^1$ is hydrogen or a group of formula

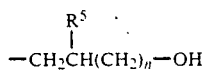

(a)

n is the number 0 or 1;
$R^2$ and $R^5$ are phenyl, m-halophenyl, m-trifluoromethylphenyl, thienyl or pyridyl;
$R^3$ hydrogen or methyl;
$R^4$ is hydrogen, $-CH_2COOH$, $-CH_2COO-C_{1-4}$-alkyl, $-(CH_2)_2O-C_{1-4}$-alkyl or $-(CH\ )_2O(CH_2)_{1-4}-C_6H_5$;
and a physiologically compatible salt thereof.

The invention also relates to processes for the preparation of these propanolamine derivatives, pharmaceutical preparations and feedstuffs containing the derivatives, and methods of using the propanolamine derivatives.

DETAILED DESCRIPTION OF THE INVENTION

The propanolamine derivatives of the present invention are compounds of formula

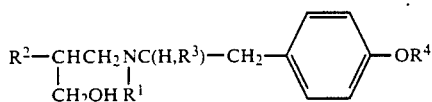

I wherein
$R^1$ is hydrogen or a group of formula

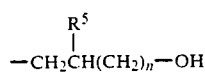

(a)

n is the number 0 or 1;
$R^2$ and $R^5$ are phenyl, m-trifluoromethylphenyl, thienyl or pyridyl;
$R^3$ or methyl;
$R^4$ is hydrogen, $-CH_2COOH$, $-CH_2COO-C_{1-4}$-alkyl, $-(CH_2)_2O-C_{1-4}$-alkyl or $-(CH_2)_2O(CH_2)_{1-4}-C_6H_5$;
and a physiologically compatible salt thereof.

The term "$C_{1-4}$-alkyl" denotes straight-chain or branched residues with 1-4 C-atoms such as methyl, ethyl, propyl, isopropyl, butyl and isobutyl.

The term "halogen" refers to bromine, chlorine, fluorine and iodine.

The term "m-halophenyl" refers to a phenyl group substituted with bromo-, chloro-, fluoro- and iodo- in the meta position.

m-Chlorophenyl is preferred among the m-halophenyl groups $R^2$ or $R^5$, and 2-thienyl and, respectively. 2-pyridyl are preferred under the thienyl and pyridyl groups.

The compounds of formula I form salts with acids, and these salts are also an object of the invention. Examples of such salts are salts with physiologically compatible mineral acids such as hydrochloric acid, hydrobromic acid, sulfuric acid, phosphoric acid; or with organic acids such as oxalic acid, methanesulfonic acid, acetic acid, propionic acid, citric acid, maleic acid, succinic acid, maleic acid, fumaric acid, phenylacetic acid or salicylic acid. Carboxylic acids of formula I can also be present as physiologically compatible salts. Examples of such salts are alkali metal, alkaline earth metal, ammonium and ethanolammonium salts.

The compounds in accordance with the invention contain at least one asymmetric carbon atom and can accordingly be present as optically active enantiomers, as diastereomers or as racemates.

Among the compounds of formula I there are preferred those in which $R^1$ is hydrogen, $R^2$ is phenyl, m-halophenyl, especially m-chlorophenyl, or m-trifluoromethylphenylphenyl, thienyl or pyridyl, especially 2- or 3-pyridyl, $R^4$ is hydrogen, 2-ethoxyethyl. 2-phenethoxyethyl or ethoxycarbonylmethyl, especially those in which the C-atom attached to a methyl group $R^3$ which may be present has the R-configuration. Those compounds in which $R^2$ is phenyl or 2-thienyl and $R^4$ is 2-ethoxyethyl or ethoxyphenyl carbonylmethyl are especially preferred. The following are examples of such compounds
(R or S)-β-[[[p-(2-ethoxyethoxy)phenethyl]amino]-methyl]phenethyl alcohol.
ethyl [p-[2-[[β-(hydroxymethyl)phenethyl]amino]-ethyl]phenoxy]acetate,
β-[[[(R)-p-(2-ethoxyethoxy)-α-methylphenethyl-]amino]methyl]phenethyl alcohol and
β-[[[p-(2-ethoxyethoxy)phenethyl)amino]methyl)-2-thiophenethanol.

Further, there are preferred the compounds of formula I in which $R^1$ represents a group of formula (a) in which either n is the number 1 and $R^5$ is phenyl or m-halophenyl, especially m-chlorophenyl, or n is the number 0 and $R^5$ is phenyl, especially in which the C-atom attached to the group $R_5$ has the R-configuration, $R^2$ is phenyl or m-halophenyl, especially m-chlorophenyl, $R^3$ is hydrogen and $R^4$ ethyl, for example.
(RS)-m-chloro-β-[p-(2-ethoxyethoxy)phenethyl][[[(R)-β-hydroxyphenethyl]amino]methyl]phenethyl alcohol.

The propanolamine derivatives of the present invention can be prepared according to methods known in the art by
(a) reducing an amide of the formula

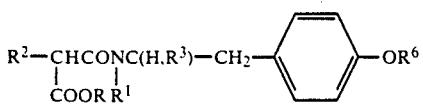

or

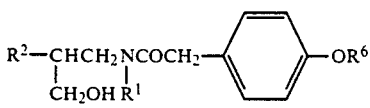

wherein $R^1$, $R^2$ or $R^3$ are as described above and $R^6$ is hydrogen, $-(CH_2)_2O-C_{1-4}$-alkyl or $-(CH_2)_2O(CH_2)_{1-4}-C_6H_5$, and (b) if desired, etherifying a phenol of formula I in which $R^4$ is hydrogen to a compound of formula I in which $R^4$ is a group $-CH^2-COOH$ or $-CH_2COO-C_{1-4}$-alkyl and (c) if desired, converting a compound of formula I into a physiologically compatible salt.

The reduction according to process variant (a) can be carried out conveniently by means of a complex metal hydride such as lithium aluminium hydride (LiAlH$_4$) in a solvent such as an ether, for example, diethyl ether, monoglyme, diglyme or tetrahydrofuran (THF), at a temperature up to the reflux temperature of the reaction mixture, preferably at room temperature.

The etherification according to variant b) can be carried out with a compound of the formula X-R$^{40}$ in which R$^{40}$ is a group $-CH^2COOH$ or $-CH_2COO-C_{1-4}$-alkyl and X is halogen, conveniently iodine, or a sulfonate group, for example, methanesulfonate. The reaction is conveniently carried out in a solvent such as a ketone, for example, acetone, an ether such as THF or in dimethylformamide in the presence of a base such as an alkali metal hydroxide, for example, potassium hydroxide or sodium hydroxide, at a temperature up to the reflux temperature, preferably at room temperature.

The amides of formulas II and III may be prepared according to methods known in the art.

Thus, the amides II are obtained by reacting an amine of formula

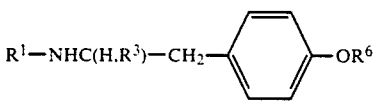

with a diester of formula $R^2-CH(COOR)_2$   V wherein R is $C_{1-4}$-alkyl

Amides of formula II in which $R^1$ is a group (a) can also be obtained by reacting a secondary amine of formula I in which $R^1$ is hydrogen with a diester V.

These reactions can be carried out in a solvent such as an ether, for example, diglyme, at temperatures up to the reflux temperature, conveniently at about 90°–100° C.

For the preparation of the amide starting material of Example 1 hereinafter, a solution of diethyl phenylmalonate in 50 mg of diglyme was treated in the manner described above with 25 g of p-(2-ethoxyethoxy)-phenerhylamine and stirred at 95° C. for 48 hrs. After cooling the excess solvent was evaporated. The residue was chromatographed on silica gel with ethyl acetate/hexane (1:2). There was obtained ethyl [[[p-(2-ethoxyethoxy)-phenethyl]carbamoyl]phenyl]acetate. m.p. 80° C. The amide starting materials of Examples 2a), 21) and 2o) described infra were also obtained in crystalline form (m.p. 108° C., 94°–95° C. and 110°–111° C., respectively).

The amides III are obtained by reacting an alcohol of formula

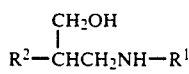

with a compound of formula

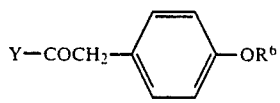

wherein Y is halogen, especially chlorine, or loweralkoxy.

This reaction can be carried out in the same manner as the reaction of an amine IV with a diester V described above.

For the preparation of the amide starting materials III of Examples (3a) and (3b), 50 g of ethyl p-(2-ethoxyethoxy)phenyl acetate in 50 ml of diglyme were treated slowly with 25 g of (R or S)-β-(aminomethyl)phenethyl alcohol and stirred at 95° C. for 48 hrs. The mixture was then cooled and evaporated and the residue was chromatographed on silica gel with ethyl acetate/hexane (1:2).

The alcohols VI can be prepared by reducing the corresponding acids of formula

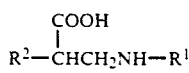

This reduction can be carried out analogously to the reduction of the amide II or III described above.

A racemate of formula VI can be resolved readily by salt formation with an optically active acid such as L- or D-dibenzoyltartaric acid and is therefore especially suitable as an intermediate in the preparation of optically active compounds III and I.

For the preparation of the alcohols VI used in Examples (3a) and (3b). 10 g of 3-amino-2-phenylpropanecarboxylic acid in 150 ml of monoglyme were stirred with 3 g of LiAlH$_4$ for 20 hrs. Then, 12 ml of water and 3 ml of 10% sodium hydroxide solution were slowly added thereto. The mixture was filtered and the filtrate was again evaporated with toluene. There was obtained 8.4 g of β-(aminomethyl)-phenethyl alcohol.

For the preparation of the R- and S-enantiomers of the β-(aminomethyl)phenethyl alcohol, the alcohol was dissolved in 200 ml of THF and treated with a solution of dibenzoyl-L-tartaric acid. After one day crystals were removed by filtration and recrystallized from ethanol until the rotation was constant. There was obtained (R or S)-β-(aminomethyl)phenethyl alcohol (S.S)-2,3-di-O-benzoyltartrate. m.p. 172°–173° C., [α]D -28.4° (DMSO, c=1%).

The mother liquors were treated with a strongly basic ion exchanger, filtered and evaporated. The oily residue of the free amine enriched with the enantiomers was treated as described above, but this time with dibenzoyl-D-tartaric acid. There was obtained (R or S)-β-(aminomethyl)phenethyl alcohol (R.R)-2.3-di-O-benzoyltartrate, m.p. 172°-173° C., $[\alpha]_D + 28.2°$ (DMSO, c=1%).

The compounds IV, V, VII and VIII, insofar as they are not known, can be prepared according to methods known in the art, as for example, by methods for preparing analogous compounds IV, V. VII and VIII which are known in the art. Thus, the diesters V can be obtained from the corresponding acetic acid esters according to the methods described in Organic Synthesis. Collective Vol. 2, Edited by A. H. Blatt (1943) 288-289.

EFFECT OF THE NOVEL PROPANOLAMINE DERIVATIVES

The propanolamine derivatives in accordance with the invention can be used as active substances in pharmaceutical preparations for the treatment of obesity and/or of diabetes mellitus, especially of obese adult diabetics. In animal experiments an increased energy expenditure, primarily fueled by catabolism of body fat, has been observed upon the aministration of the said derivatives. Furthermore, the propanolamine derivatives in accordance with the invention stimulate the formation of brown adipose tissue.

It is known that defects of the brown adipose tissue play a substantial role in the origin of obesity. In obese-hyperglycemic mice and in streptozotocin-diabetic rats these derivatives have a pronounced antidiabetic effect, in that they have hypoglycemic activity and reduce glycosuria.

The propanolamine derivatives in accordance with the invention exhibit only a slight activity on the working of the heart and circulation. Moreover, they have only a slight activity on insulin secretion. This is of significance, since as is known high plasma insulin plays an important role in the pathogenesis of obesity. The dosage can amount to 0.5-1000 mg. preferably 2.200 mg, per day for an adult depending on the strength of activity of the individual compounds and on the individual requirements of the patients, whereby the dosage can be administered as a single dosage or in several dosages over the day.

In addition, the propanolamine derivatives in accordance with the invention lead to an increase in the body protein content and a decrease in the body fat content. The said derivatives therefore lead to an increase in the lean composition of the body at the expense of fat. Accordingly, they can be used in human medicine for the treatment of conditions which are associated with high protein breakdown, for example, in convalescence after operations. In this case the dosages administered are the same as in the treatment of obesity and/or of diabetes mellitus.

The propanolamine derivatives in accordance with the invention can also be used in the maintenance of meat producing animals such as beef cattle, pigs, sheep and poultry. As the said derivatives increase body protein while reducing body fat they provide a method for improving the weight gain and/or improving the feed utilization efficiency and/or increasing lean body mass. In this case the dosage forms are the same as in the case of vitamins. The said derivatives can also be used as feed additives in dosages of 0.01-100 mg/kg depending on the substance, kind of animal and age.

The pharmaceutical preparations contain the active substances together with a compatible pharmaceutical, organic or inorganic carrier material such as water, gelatin, gum arabic, lactose, starch, magnesium stearate, talc, vegetable oils, polyalkylene glycols or white petroleum jelly such as Vaseline ®.

The pharmaceutical preparations are preferably administered orally, for example, in the form of tablets, capsules, pills, powders, granulates, solutions, syrups, suspensions or elixirs. The administration can, however, also be effected parenterally, for example, in the form of sterile solutions, suspensions or emulsions. The pharmaceutical preparations can be sterilized and may contain ingredients such as preserving agents, stabilizing agents, wetting agents, emulsifiers, salts for varying the osmotic pressure and buffer substances.

The useful activity of the novel compounds of formula I is evident from the following test results:

MATERIALS AND METHODS (1) -Activity on oxygen consumption

Male albino rats weighing 160-180 g were placed in metabolic cages after fasting for 24 hours. The cages were ventilated with a constant 6 liter room air/minute which was equilibrated at a dew point of 11° C. Samples of the spent air were collected during periods of in each case 14 minutes after again equilibrating and the oxygen content and $CO_2$ content were analyzed. After an adaptation time of 4 hours the animals, divided into groups of 6, received either placebo (5% gum arabic) or the test substance (suspended in 5% gum arabic) per os. Thereafter, the determinations were carried out for a period of 12 hours. In Table I the average oxygen consumption after medication during the first 3 hours and the entire test duration (12 hours) is given as percentage of the oxygen consumption during the adaptation period. Corresponding corrections for changes in the placebo group have been taken into consideration.

TABLE 1

| Compound of Example No. | Dosage μM/kg | $O_2$ consumption % of the value of the pre-period | |
|---|---|---|---|
| | | 1st-3rd hour | 1st-12th hour |
| 2a | 10 | 149 | 113 |
| 2b | 3 | 124 | 107 |
| 2c | 3 | 132 | 108 |
| 2d | 3 | 152 | 127 |
| 2j | 10 | 137 | 113 |
| 2o | 10 | 147 | 115 |
| 3a | 3 | 152 | 112 |
| 4 | 3 | 145 | 112 |

(2) Activity on heart rate

Male albino rats weighing 250-320 g received 6 hours after withdrawl of food either placebo (5% gum arabic) or the test substance (suspended in 5% gum arabic) per os. The animals were subsequently immobilized in perforated plastic tubes. The electrocardiogram was derived by means of bipolar subcutaneous needle electrodes. The R-peak was used to trigger a beat counter. The heart rate measured 1 and 3 hours after treatment was given in Table II as a percentage of the control value (placebo).

TABLE II

| Compound of Example | Dosage (mg/kg) | Heart rate (% of controls) | |
|---|---|---|---|
| | | 1 hour | 3 hours |
| 2a | 30 | 105 | 100 |

TABLE II-continued

| Compound of Example | Dosage (mg/kg) | Heart rate (% of controls) | |
|---|---|---|---|
| | | 1 hour | 3 hours |
| | 100 | 121 | 112 |
| 2b | 30 | 106 | 99 |
| | 100 | 114 | 105 |
| 2c | 10 | 103 | 102 |
| | 30 | 111 | 104 |
| 2d | 10 | 103 | 100 |
| | 30 | 111 | 104 |
| 2j | 100 | 110 | — |
| 2o | 30 | 108 | — |
| | 100 | 111 | |
| 3a | 10 | 108 | — |
| | 30 | 115 | — |

CONCLUSION

The data indicate that the novel propanolamine derivatives potently increase energy expenditure as demonstrated by the stimulation of O₂ consumption. In contrast, the said derivatives only at high dosage exhibit slight activity on the working of the heart.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, precentages and ratios relating to solvent mixtures are expressed in volume, purity data determined by gas chromatography are expressed in area %, and the remaining percentages and ratios are expressed in weight. Temperatures are in degrees Celsius (° C), normal pressure is about 1 atmosphere, and room temperature is about 23° C. Examples were carried out as written unless indicated otherwise.

EXAMPLE 1

A solution of 15 g of LiAlH₄ in 600 ml of diethyl ether was treated while stirring with a solution of 20 g of ethyl [[[p-(2-ethoxyethoxy)phenethyl]carbamoyl]-phenyl]-acetate. After stirring for 12 hours 15 ml of water and 5 ml of 10% sodium hydroxide solution were added to the mixture. The mixture was filtered through silica gel and the filtrate was evaporated. The residue was dissolved in ethanol and treated with the equivalent amount of oxalic acid dissolved in ethanol. After adding ethyl acetate there was obtained β-[[[p-(2-ethoxyethoxy)phenethyl]amino]methyl]phenethyl alcohol oxalate m.p. 145° C.

EXAMPLE 2

In a manner analogous to the methods described in Example 1 above.

(2a) from ethyl [[(R)-p-(2-ethoxyethoxy)-α-methylphenethyl]carbamoyl]phenylacetate there was prepared β-[[[(R)-p-(2-ethoxyethoxy)-α-methylphenethyl]amino]-methyl]-phenethyl alcohol oxalate m.p. 145° C. (decomposition).

(2b) from ethyl [[p-(2-ethoxyethoxy)phenethyl]carbamoyl]-m-chlorophenylacetate there was prepared m-chloro-β-[[[p-(2-ethoxyethoxy)phenethyl]amino]methyl]phenethyl alcohol oxalate m.p. 148° C.

(2c) from (RS)-2-phenyl-N-[(RS)-β-(hydroxymethyl)phenethyl]-N-[p-(2-ethoxyethoxy)phenethyl]ethylmalonamate there was prepared β, β'-8 [[p-(2-ethoxyethoxy)phenethyl]-imino]dimethylene]-bis-[(RS)-phenethyl alcohol]hydrochloride m.p. 94° C.

(2d) from (RS)-2-(m-chlorophenyl)-N-[p-(2-ethoxyethoxy)phenethyl]-N-[(R)-β-hydroxyphenethyl]-malonamate there was prepared (RS)-m-chloro-β-[p-(2-ethoxyethoxy)phenethyl][[[(R)-β-hydroxyphenethyl]amino)methyl]phenethyl alcohol oxalate m.p. 130° C.

(2e) from ethyl (RS)-[[[(R)-α-methyl-p-(2-phenethoxy)ethoxy]phenethyl]carbamoyl]-m-chlorophenyl acetate there was prepared (RS)-m-chloro-β-[[[(R)-α-methyl-p-[2-(phenethoxy)ethoxy]phenethyl]amino]methyl]phenethyl alcohol oxalate m.p. 164°–166° C.

(2f) from (RS)-2-(m-chlorophenyl)-N-[(RS)-m-chloro-β-(hydroxymethyl) phenethyl]-N-[p-(2-ethoxyethoxy)phenethyl]ethylmalonamate there was prepared β, β'-[[[p-(2-ethoxyethoxy)phenethyl]imino]dimethylene]-bis[(RS)-m-chlorophenethyl alcohol]hydrochloride m.p. 148° C.

(2g) from ethyl (RS)-[[[(R)-α-methyl-p-(2-ethoxyethoxy)-phenethyl]carbamoyl]-m-chlorophenyl acetate there was prepared (RS)-m-chloro-β-[[[(R) p-(2-ethoxyethoxy)-α-methyl-phenethyl]amino]-methyl]phenethyl alcohol oxalate m.p. 145° C.

(2h) from ethyl [[p-hydroxyphenethyl]carbamoyl]-phenyl acetate there was prepared β-[[(p-hydroxyphenethyl)amino]methyl]-phenethyl alcohol oxalate m.p. 136°–137° C.

(2i) from ethyl (RS)-[[[(R) α-methyl-p-(2-phenethoxy)-ethoxy]phenethyl]carbamoyl]phenyl acetate there was prepared β-[[[(R)-α-methyl-p-(2-phenethoxy)ethoxy]phenethyl]amino]-methyl]phenethyl alcohol oxalate m.p. 165°–179° C.

(2j) from ethyl [[p-(2-phenethoxy)ethoxy]phenethyl]-carbamoyl]phenyl acetate there was prepared β-[[[p-(2-phenethoxy)ethoxy]phenethyl]amino]methyl]phenethyl alcohol oxalate m.p. 145° C.

(2k) from ethyl [[p-(2-ethoxyethoxy)phenethyl]carbamoyl]-m-trifluoromethylphenyl acetate there was prepared β-[[[p-(2-ethoxyethoxy) phenethyl]amino]methyl]-m trifluoromethylphenethyl alcohol oxalate m.p. 148° C.

(2l) from ethyl α-[[p-(2-ethoxyethoxy)phenethyl]carbamoyl]-3-thiopheneacetate there was prepared β-[[[p-(2-ethoxyethoxy)phenethyl]amino]methyl]-3-thiophene-ethanol oxalate m.p. 153°–155° C.

(2m) from ethyl α-[[p-(2-ethoxyethoxy)phenethyl]carbamoyl]-2-pyridine acetate there was prepared β-[[[p-(2-ethoxyethoxy)phenethyl]amino]methyl]-2-pyridine-ethanol oxalate m.p. 128°–129° C.

(2n) from ethyl α-[[p-(2-ethoxyethoxy)phenethyl]carbamoyl]-3-pyridineacetate there was prepared B-[[[p(2-ethoxyethoxy)phenethyl]amino]methyl]-3-pyridine-ethanol oxalate m.p. 170° C. (decomposition).

(2o) from ethyl α-[[p-(2-ethoxyethoxy)phenethyl]carbamoyl]-2-thiopheneacetate there was prepared β-[[[p-(2-ethoxyethoxy)phenethyl]amino]methyl]-2-thiophene-ethanol oxalate m.p. 145° C. (decomposition).

EXAMPLE 3

Analogously to Example 1, (3a) from N-[(R or S)-3-hydroxy-2-phenylpropyl]-p-(2-ethoxyethoxy)phenylacetamide there was prepared (R or S)-β-[[[p-(2-ethoxyethoxy)phenethyl]amino]methyl]-phenethyl alcohol oxalate m.p. 152°-154° C., $[\alpha]_D$ −9° (DMSO, c=1%)

(3b) from the enantiomer corresponding to Example 3a) there was prepared the enantiomer (R or S)-β-[[[p-(2-ethoxyethoxy)phenethyl]amino]methyl]-phenethyl alcohol oxalate m.p. 151°-154° C. $[\alpha]_D$ +8 3° (DMSO, c=1%).

EXAMPLE 4

3.62 g of the product of Example 2h) were stirred for 24 hours in 200 ml of acetone with 2.5 g of ethyl iodoacetate and 2 g of potassium hydroxide. The mixture was then evaporated, the residue was taken up in water and ethyl acetate. The organic phase was separated, dried over sodium sulfate and evaporated. The residue was chromatographed on silica gel. The product was dissolved in ethanol, treated with 1 ml of concentrated hydrochloric acid and evaporated with ethanol. Crystallization of the residue from ethanol/ ether gave ethyl [p-[2-[[β-(hydroxymethyl)phenethyl]-amino]ethyl]-phenoxy]acetate hydrochloride m.p. 104°-105° C.

EXAMPLE 5

An oral dosage formulation of the following composition is prepared as follows:

| | | |
|---|---|---|
| 1. | Active substance of formula I, for example, (RS)-m-chloro-β-[p-(2-ethoxyethoxy)-phenethyl][[[(R)-β-hydroxyphenethyl]-amino]methyl]phenethyl alcohol oxalate | 250 mg |
| 2. | Lactose | 200 mg |
| 3. | Maize starch | 300 mg |
| 4. | Maize starch paste | 50 mg |
| 5. | Calcium stearate | 5 mg |
| 6. | Dicalcium phosphate | 45 mg |

Manufacturing Procedure

A. Mix 1 with 2 to form mixture.

B. Add 3-6, and mix thoroughly with mixture prepared in step A.

C. Pass through a suitable mill and fill capsules with formulation or press formulation into tablet form.

We claim:

1. A compound of the formula

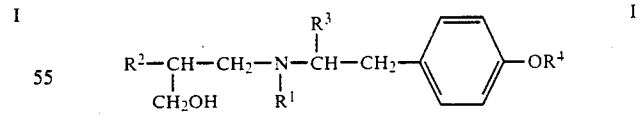

I wherein
R$^1$ is hydrogen or a group of formula

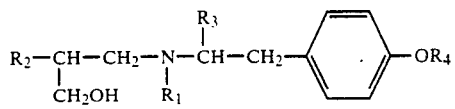

(a)

n is the number 0 or 1;
R$^2$ and R$^5$ are phenyl, m-halophenyl or m-trifluoromethylphenyl;
R$^3$ is hydrogen or methyl;
R$^4$ is hydrogen, —CH$_2$COOH, —CH$_2$COO—C$_{1-4}$-alkyl, —(CH$_2$)$_2$O—C$_{1-4}$-alkyl or —(CH$_2$)$_2$O(CH$_2$)$_{1-4}$—C$_6$H$_5$;
or a physiologically compatible salt thereof.

2. A compound according to claim 1 wherein R$^1$ is hydrogen.

3. A compound according to claim 1, wherein R$^1$ is the group (a); and n is the number 0 or 1.

4. A compound according to claim 1, wherein R$^1$ is hydrogen and R$^4$ is hydrogen, 2-ethoxyethyl or 2-phenyethoxyethyl.

5. A compound according to claim 4, wherein R$^2$ is m-chlorophenyl.

6. A compound according to claim 4, wherein R$^2$ is phenyl and R$^4$ is 2-ethoxyethyl or ethoxy-carbonylmethyl.

7. A compound according to claim 6, selected from the group consisting of;
(R or S)-(GL)β-[[[p-(2-ethoxyethoxy)phenethyl]amino]methyl]-phenethyl alcohol,
ethyl [p-[2-[[β-(hydroxymethyl[phenethyl]amino]ethyl]-phenoxy]acetate, and
β[[[(R)-p-(2-ethoxyethoxy)-α-methylphenethyl]amino[methyl]phenethyl alcohol.

8. A compound according to claim 1 wherein R$^3$ is methyl and a C-atom of the compound attached to the methyl group of R$^3$ has a R-configuration.

9. A compound according to claim 1, wherein R$^1$ is the group of the formula (a): n is the number 1; R$^2$ is phenyl or m-halophenyl; R$^3$ is hydrogen, R$^4$ is 2-ethoxyethyl; and R$^5$ is phenyl or m-halophenyl.

10. A compound according to claim 9 wherein R$^5$ is m-chlorophenyl.

11. A compound according to claim 9 wherein n is the number 0; and R$^5$ is phenyl.

12. A compound according to claim 11 wherein a C-atom of the compound of formula I attached to the R$^5$ has a R configuration.

13. A compound according to claim 9, wherein R$^2$ is m-chlorophenyl.

14. A compound according to claim 9, wherein R$^1$ is β-hydroxyphenethyl and R$^2$ is m-chlorophenyl.

15. A compound according to claim 14 wherein R$^1$ is (R)-β-hydroxylphenethyl.

16. A compound according to claim 1, (RS)-m-Chloro-β-[p-(2-ethoxyethoxy)phenethyl] [[[(R)-β-hydroxyphenethyl]-amino]methyl]phenethyl alcohol.

17. A composition for treating obesity or diabetes mellitus comprising:

a) a compound of the formula

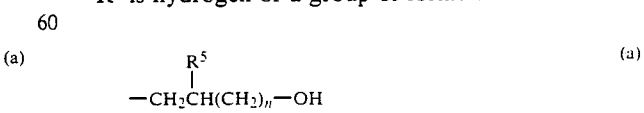

I wherein
R$^1$ is hydrogen or a group of formula

(a)

n is the number 0 or 1;
R$^2$ and R$^5$ are phenyl, m-halophenyl or m-trifluoromethylphenyl;
R$^3$ is hydrogen or methyl;

$R^4$ is hydrogen, $-CH_2COOH$, $-CH_2COO-C_{1-4}$-alkyl, $-(CH_2)_2O-C_{1-4}$-alkyl or $-(CH_2)_2O(CH_2)_{1-4}-C_6H_5$;

or a physiologically compatible salt thereof, in an amount which is effective in treating obesity or diabetic mellitus, and b) a pharmaceutically acceptable carrier.

18. A composition according to claim 17 wherein the carrier is suitable for oral administration of the composition.

19. A method for treating obesity, or diabetes mellitus in a patient in need of such treatment comprising: administering a compound of the formula

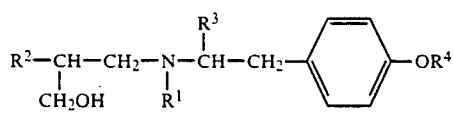

wherein
$R^1$ is hydrogen or a group of formula

n is the number 0 or 1;
$R^2$ and $R^5$ are phenyl, m-halophenyl, m-trifluoromethylphenyl;
$R^3$ is hydrogen or methyl;
$R^4$ is hydrogen, $-CH_2COOH$, $-CH_2COO-C_{1-4}$-alkyl, $-(CH_2)_2O-C_{1-4}$-alkyl or $-(CH_2)_2O(CH_2)_{1-4}-C_6H_5$;

or a physiological compatible salt thereof, in an amount effective for treating obesity or diabetes mellitus.

20. A composition for fattening animals comprising:
a) an effective amount to fatten animals of a compound of the formula

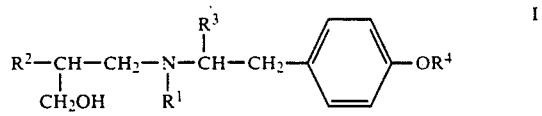

wherein
$R^1$ is hydrogen or a group of formula

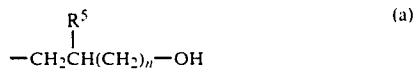

n is the number 0 or 1;
$R^2$ and $R^5$ are phenyl, m-halophenyl or m-trifluoromethylphenyl;
$R^3$ is hydrogen or methyl;
$R^4$ is hydrogen, $-CH_2COOH$, $-CH_2COO-C_{1-4}$-alkyl, $-(CH_2)_2O-C_{1-4}$-alkyl or $-(CH_2)_2O(CH_2)_{1-4}-C_6H_5$;

or a physiologically compatible salt thereof, and
b) a compatible carrier material.

* * * * *

UNITED STATES PATENT AND TRADEMARK OFFICE
CERTIFICATE OF CORRECTION

PATENT NO.   : 5,045,567
DATED        : September 3, 1991
INVENTOR(S)  : Frank Kienzle It is certified that error appears in the above-identified patent and that said Letters Patent is hereby corrected as shown below:

On the Title Page, under Foreign Application Priority Data, [30], the filing date for Swiss Application No. 2245/88 should read June 10, 1988.

In claim 7, column 10

Line 21:    "(hydroxymethyl[phenethyl]" should read

-- (hydroxymethyl)phenethyl] --

Line 23:    "ß[[" should read   -- ß-[[ --.

Signed and Sealed this

Nineteenth Day of January, 1993

*Attest:*

DOUGLAS B. COMER

*Attesting Officer*      *Acting Commissioner of Patents and Trademarks*